(12) United States Patent
Black et al.

(10) Patent No.: US 7,705,010 B2
(45) Date of Patent: Apr. 27, 2010

(54) USE OF MINOXIDIL SULFATE AS AN ANTI-TUMOR DRUG

(75) Inventors: Keith L. Black, Los Angeles, CA (US); Christopher Wheeler, Newbury Park, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 250 days.

(21) Appl. No.: 11/813,461

(22) PCT Filed: Feb. 22, 2006

(86) PCT No.: PCT/US2006/006088

§ 371 (c)(1),
(2), (4) Date: Jul. 6, 2007

(87) PCT Pub. No.: WO2006/091587

PCT Pub. Date: Aug. 31, 2006

(65) Prior Publication Data

US 2008/0207657 A1    Aug. 28, 2008

Related U.S. Application Data

(60) Provisional application No. 60/655,009, filed on Feb. 22, 2005.

(51) Int. Cl.
*A61K 31/506* (2006.01)
(52) U.S. Cl. ........................................... 514/275
(58) Field of Classification Search .................. 514/275
See application file for complete search history.

(56) References Cited

U.S. PATENT DOCUMENTS

| 3,461,461 | A | * | 8/1969 | Anthony et al. | 544/323 |
|---|---|---|---|---|---|
| 4,287,338 | A | * | 9/1981 | McCall | 544/123 |
| 4,912,111 | A | * | 3/1990 | Sank et al. | 514/256 |
| 5,360,804 | A | * | 11/1994 | Gaetani et al. | 514/245 |
| 5,654,337 | A | | 8/1997 | Roentsch et al. | |
| 6,136,860 | A | * | 10/2000 | Rushton | 514/561 |
| 7,018,979 | B1 | * | 3/2006 | Black et al. | 514/1 |
| 7,442,369 | B1 | * | 10/2008 | Pena et al. | 424/70.1 |
| 2002/0028808 | A1 | | 3/2002 | Hansen | |
| 2002/0137692 | A1 | * | 9/2002 | Rundegren et al. | 514/27 |
| 2003/0072748 | A1 | | 4/2003 | Black et al. | |
| 2003/0215528 | A1 | | 11/2003 | Graham et al. | |

FOREIGN PATENT DOCUMENTS

| DE | 3331459 A1 | 3/1984 |
|---|---|---|
| WO | 97/18332 A1 | 5/1997 |
| WO | WO 01/54771 A2 * | 8/2001 |
| WO | 2005/043155 | 5/2005 |
| WO | 2006/036278 A2 | 4/2006 |

OTHER PUBLICATIONS

Sausville et al. Cancer Research, 2006, vol. 66, pp. 3351-3354.*
Johnson et al. British J. of Cancer, 2001, 84(10):1424-1431.*
Wondergem et al. J. Membr. Biol., 1998, vol. 161, No. 3, pp. 257-262 (Abstract attached).*
Abdul et al. Cancer Lett., 2002, vol. 186, No. 1, pp. 99-105 (Abstract attached).*
Abdul et al. Oncol. Rep., 2002, vol. 9, No. 5, pp. 961-964 (Abstract attached).*
Abdul et al. Anticancer Res., 2003, vol. 23, No. 4, pp. 3347-3351 (Abstract attached).*
Takeda et al. Tokai J. Exp. Clin. Med., 1991, vol. 16, No. 1, pp. 73-76 (Abstract attached).*
Lee et al., In Vitro Antitumor Activity of Cromakalim in Human Brain Tumor Cells, Pharmacology, (1994), pp. 69-74, 49.
Ito et al., Cromakalim, A Vasodilator, Differentially Inhibits Ca2+ Currents in NG108-15 Neuroblastoma X Glioma Hybrid Cells, FEBS, (Mar. 1990), pp. 313-316, 262(2).
Ito, Y., Effects of Potassium Channel Opener Cromakalim on Calcium and Potassium Channels, Kanazawa Daigaku Juzen Igakkai Zasshi, (1992), pp. 46-56, 101(1).
Wheeler et al., Clinical Responsiveness of Glioblastoma Multiforme to Chemotherapy After Vaccination, Clinical Cancer Research, (Aug. 15, 2004), pp. 5316-5326, 10.
Kaji et al., Potassium Channel Dysfunction at the Lesion Site in Multifocal Motor Neuropathy As Revealed by Threshold Electronus, Ion Channel Media, Glia Research Portal, (1995), pp. 1368-1369, 35, Abstract Only.
Brismar et al., Potassium and Sodium Channels in Human Malignant Glioma Cells, Brain Research, (Feb. 20, 1989), pp. 259-267, 480(1-2), Abstract Only.
Tanhehco, E.T., Potassium Channel Modulators As Anti-Inflammatory Agents, Expert Opinions on Therapeutic Patents, (Jul. 1, 2001), pp. 1137-1145, 11(7).
Ningaraj et al., Adenosine 5'-Triphosphate-Sensitive Potassium Channel-Mediated Blood-Brain Tumor Barrier Permeability Increase in a Rat Brain Tumor Model, Cancer Research, (Dec. 15, 2003), pp. 8899-8911, 63.
Cohen et al., Direct Effects of Minoxidil on Epidermal Cells in Culture, Journal of Investigative Dermatology, (1984), pp. 90-93, 82.
Zhang et al., T Cell Activity in Glioma Chemoresponsiveness and Genetics, Gene Therapy and Molecular Biology, (2005), pp. 401-416, 9.

* cited by examiner

*Primary Examiner*—James D Anderson
(74) *Attorney, Agent, or Firm*—Seth D. Levy; Davis Wright Termaine LLP

(57) ABSTRACT

The invention relates to compositions, methods and kits for the treatment of cancer. ATP-dependent potassium channel agonists, salts thereof, or chemical analogs thereof, for example, minoxidil sulfate, have been found to possess antineoplastic properties. Administering minoxidil sulfate may prolong the life of a cancer patient; for example, a patient with a brain tumor.

12 Claims, 3 Drawing Sheets

USE OF MINOXIDIL SULFATE AS AN ANTI-TUMOR DRUG

Figure 1:
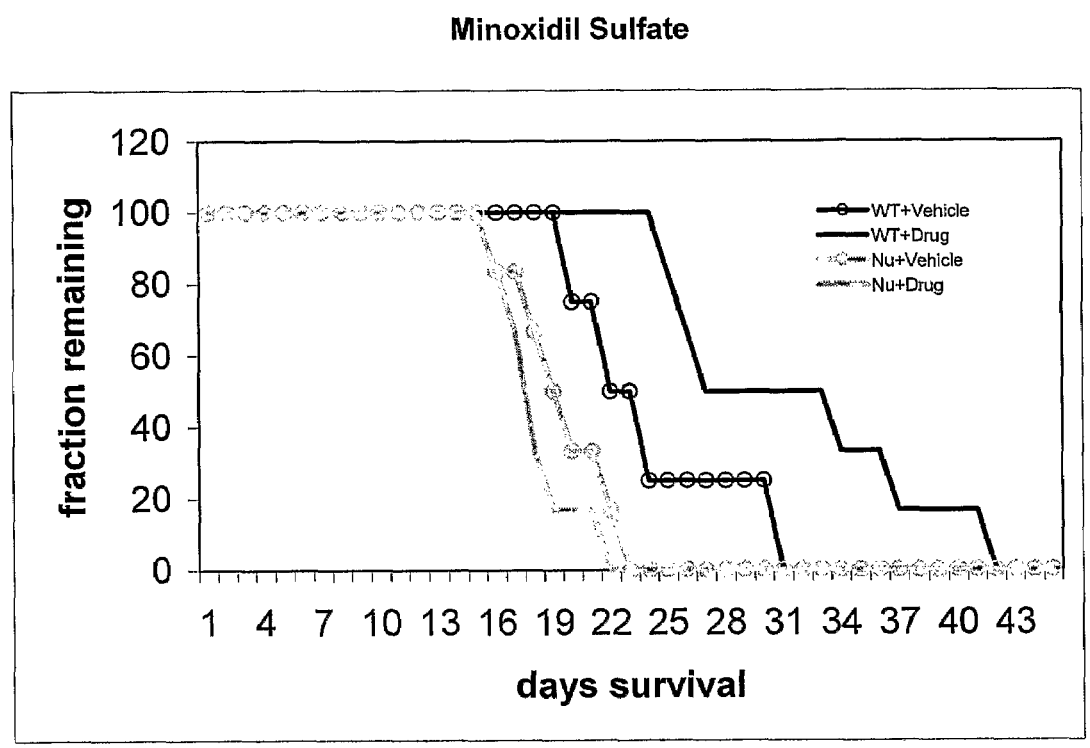

This application is the National Phase of International Application PCT/US06/06088, filed Feb. 22, 2006, which designated the U.S. and that International Application was published under PCT Article 21(2) in English. This application also includes a claim of priority under 35 U.S.C. §119(e) to U.S. provisional patent application No. 60/655,009, filed Feb. 22, 2005.

FIELD OF INVENTION

The invention relates to compositions and methods for the treatment of cancer.

BACKGROUND OF THE INVENTION

Cancer remains among the leading causes of death in the United States and around the world. Various forms of cancer are differentially treated, depending in part on the location of a tumor. One particularly difficult group of tumors to treat includes those that reside in and near the brain. Treatment of brain tumors presents a number of problems, not the least of which being the dangers inherent in any surgical procedure involving regions of the brain and the tissue located nearby. There is little room for error and the consequences of even a minor surgical mishap can be devastating to a patient; brain damage, or even death may result. Still, where possible, surgery remains the preferred method of treatment for most brain tumors and is often performed in conjunction with radiation therapy and chemotherapy. However, even commonly referenced medical authority suggests that patients with brain tumors be referred to centers specializing in investigative therapies; an indication that conventional modes of treatment are not overwhelmingly successful.

Glioblastoma multiforme ("GBM") and anaplastic astrocytomas are classified in the category of brain tumors commonly known as malignant gliomas. Although not particularly common tumors themselves, they represent a class of tumors associated with significant rates of mortality and morbidity. Current treatment for malignant glioma consists of surgical resection followed by radiation therapy and chemotherapy. However, this treatment generally fails in substantially changing the outcome for a patient; median survival remains less than one year even with medical intervention.

There remains a significant need in the art for improved methods for the treatment of cancer, and, in particular, for brain tumors.

SUMMARY OF THE INVENTION

The present invention relates to compositions, methods, and kits useful in the treatment of disease conditions such as cancer; particularly for the treatment of brain tumors. Compositions of the present invention include an ATP-dependent potassium channel ("KATP") agonist as an anti-neoplastic agent. In one embodiment, the anti-neoplastic agent is minoxidil or a salt or chemical analog thereof.

Various embodiments of the present invention provide for methods of treating cancer by administering an ATP-dependent potassium channel agonist to a mammalian subject. In a particular embodiment the mammalian subject is a human subject.

Other embodiments of the present invention contemplate using the ATP-dependent potassium channel agonist in conjunction with additional cancer therapies. The additional cancer therapies may be administered to a mammalian subject prior to, concurrently with, and/or after the administration of the ATP-dependent potassium channel agonist.

Additional embodiments provide for the administration of the ATP-dependent potassium channel agonist in conjunction with an agent to enhance the permeability of the blood-brain barrier and/or the blood-tumor barrier.

Further embodiments include administering the ATP-dependent potassium channel agonist in conjunction with vaccination therapies.

Still further embodiments provide for a kit for practicing the inventive method of administering an ATP-dependent potassium channel agonist to treat cancer in a mammalian subject.

Other features and advantages of the invention will become apparent from the following detailed description, taken in conjunction with the accompanying drawings, which illustrate, by way of example, various features of embodiments of the invention.

FIGURES

Exemplary embodiments are illustrated in referenced figures. It is intended that the embodiments and figures disclosed herein are to be considered illustrative rather than restrictive.

FIG. 1 depicts T cell-induced chemosensitization of murine glioma in accordance with an embodiment of the present invention. Fifty thousand (50,000) GL26 tumor cells in 2 ml 1% methylcellulose were implanted i.c. into anesthetized female C57BL/6J (black lines) or nu/nu (gray lines) mice aged 6-8 weeks using a stereotactic rodent frame. Injection was 1 mm posterior and 2.5 mm lateral to the junction of the coronal and saggital sutures (bregma), at a depth of 2 mm. Vaccinated mice received 2, subcutaneous injections of 2×106 tumor lysate-pulsed, irradiated cultured DC2.4 dendritic cells in 50 ml sterile PBS as vaccine on day 3 and 7 post tumor implantation, and a chemotherapeutic drug (dosage: 2.7 mg/kg minoxidil sulfate) was administered on days 7, 8, and 9 post tumor implantation. Minoxidil sulfate increased survival in C57BL/6J relative to nu/nu mice (P<0.05). Survival differences were assessed by log-rank statistics.

Figure 2A:
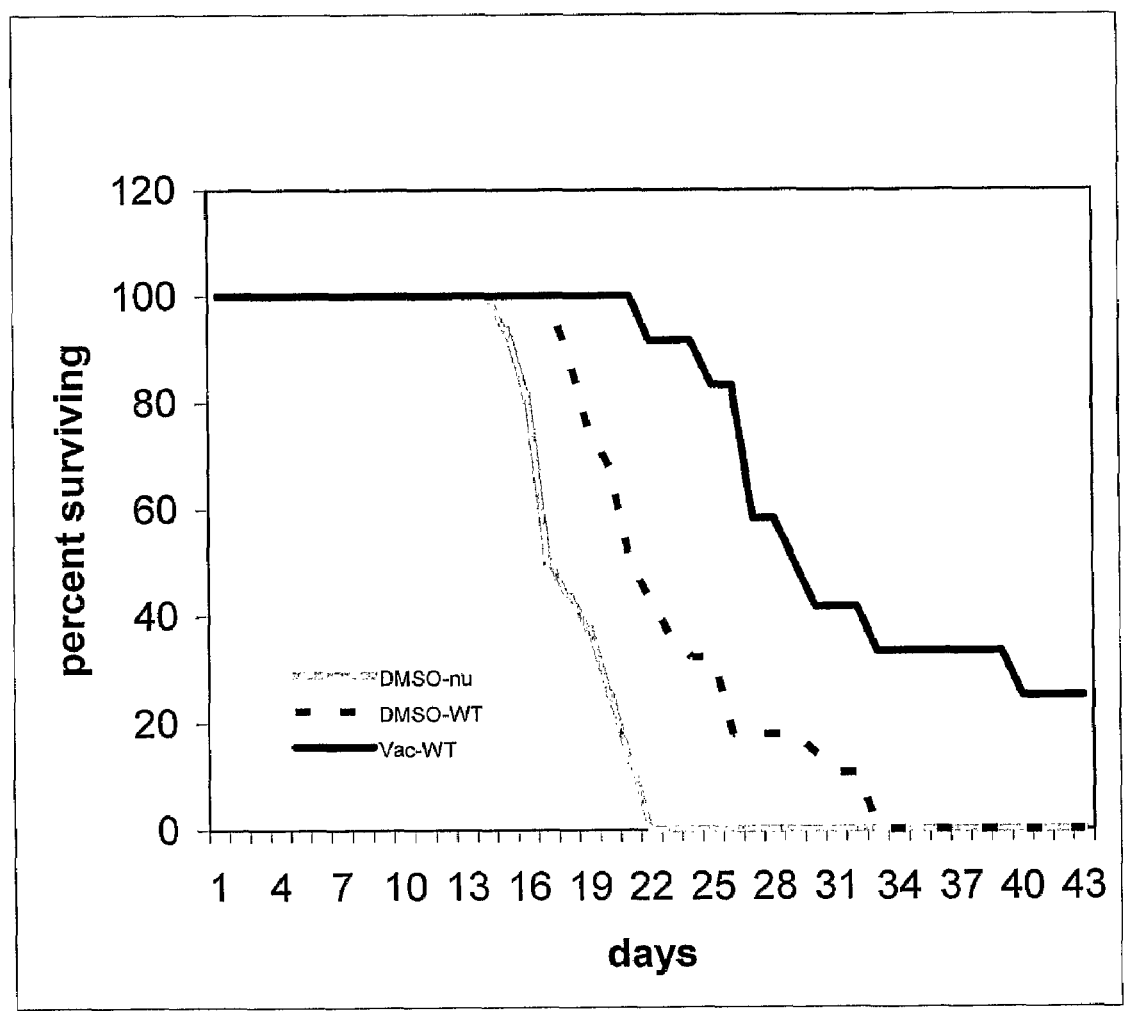
Figure 2B:
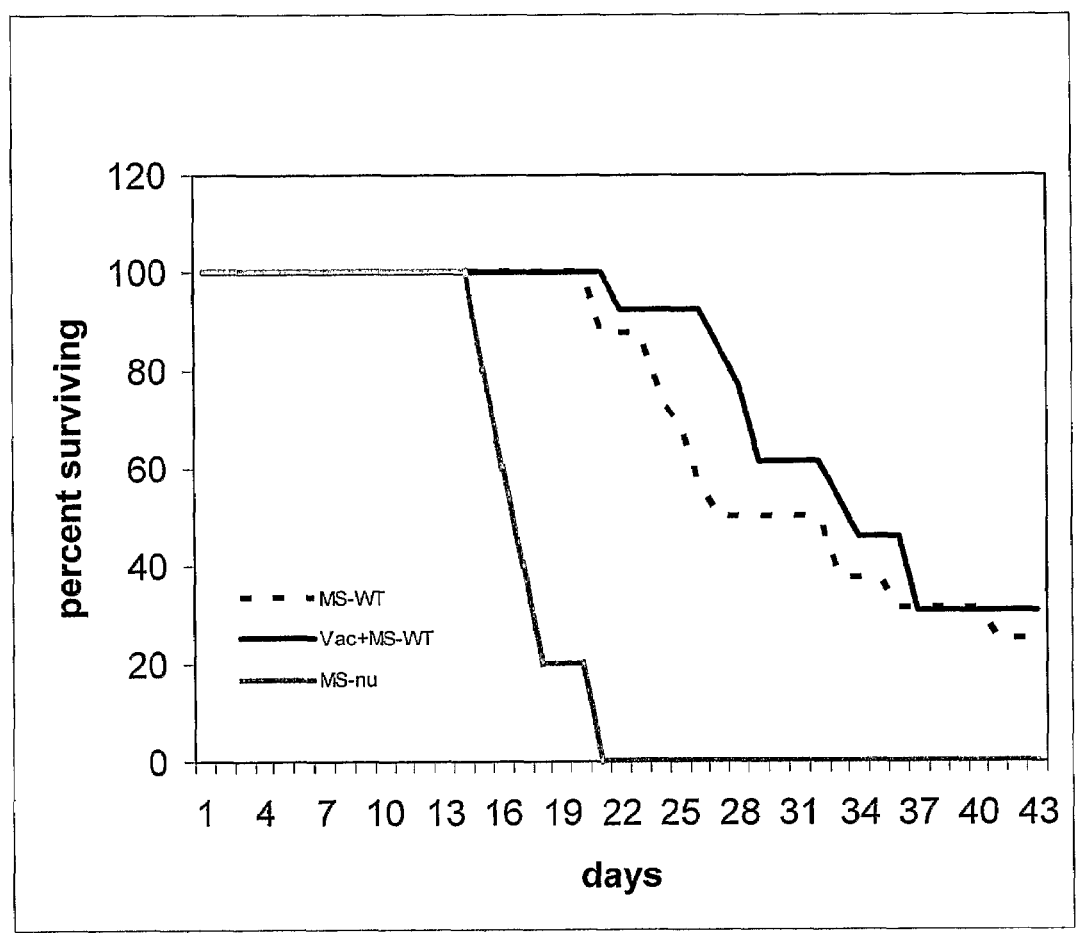

FIGS. 2a and 2b depicts survival rates of mice treated with minxodil sulfate in accordance with an embodiment of the present invention. Survival of Nude (nu; gray) and C57BL/6 (WT) mice with (solid black) or without (dotted black) vaccination, treated 7-9 days after intracranial GL26 glioma implantation with vehicle (DMSO) or minoxidil sulfate (MS, 2.7 mg/kg in 50 µl, i.v.). Vaccinated mice were injected subcutaneously with 50,000 tumor lysate-pulsed syngeneic DC2.4 dendritic cells 3 and 7 days after GL26 implantation. MS treatment increased survival only in WT hosts (P=0.001; P>0.5 for nu). WT vs. Nu survival was also significantly increased (P=0.008).

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994); March, Advanced Organic Chemistry Reactions, Mechanisms and Structure 4th ed., J. Wiley & Sons (New York, N.Y. 1992); and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Alleviating" specific cancers and/or their pathology includes degrading a tumor, for example, breaking down the structural integrity or connective tissue of a tumor, such that the tumor size is reduced when compared to the tumor size before treatment. "Alleviating" metastasis of cancer includes reducing the rate at which the cancer spreads to other organs.

"Beneficial results" may include, but are in no way limited to, lessening or alleviating the severity of the disease condition, preventing the disease condition from worsening, curing the disease condition and prolonging a patient's life or life expectancy. The disease conditions may relate to or may be modulated by the central nervous system.

"Cancer" and "cancerous" refer to or describe the physiological condition in mammals that is typically characterized by unregulated cell growth. Examples of cancer include, but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer; including, but not limited to, gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary adenomas, neuroblastomas, and craniopharyngiomas.

"Conditions" and "disease conditions," as used herein may include, but are in no way limited to any form of neoplastic cell growth and proliferation, whether malignant or benign, pre-cancerous and cancerous cells and tissues; in particular, gliomas, astrocytomas, ependymal tumors, glioblastoma multiforme, and primitive neuroectodermal tumors.

"Curing" cancer includes degrading a tumor such that a tumor cannot be detected after treatment. The tumor may be reduced in size or become undetectable, for example, by atrophying from lack of blood supply or by being attacked or degraded by one or more components administered according to the invention.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Treatment" and "treating," as used herein refer to both therapeutic treatment and prophylactic or preventative measures, wherein the object is to prevent or slow down (lessen) the targeted pathologic condition or disorder even if the treatment is ultimately unsuccessful. Those in need of treatment include those already with the disorder as well as those prone to have the disorder or those in whom the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

"Tumor," as used herein refers to all neoplastic cell growth and proliferation, whether malignant or benign, and all pre-cancerous and cancerous cells and tissues.

The composition of the present invention includes an ATP-dependent potassium channel agonist as an anti-neoplastic agent for the treatment of cancer. Minoxidil is one such agent; salts (e.g., minoxidil sulfate) and chemical analogs thereof may also be used. Oral minoxidil (2,4-pyrimidinediamine, 6-(1-piperidinyl)-,3-oxide) was originally indicated for the treatment of high blood pressure. It is a vasodilator that relaxes blood vessels. It is available, for example, under the trade name Loniten® from Pfizer, Inc. (New York, N.Y.) in various dosage formulations, although generic versions are also available. Minoxidil was later found to possess a second therapeutic characteristic: increasing hair growth. This led to the development of a topical formulation of minoxidil sulfate. The topical formulation is available, for example, under the trade name Rogaine®, also from Pfizer. Specifically, the topical formulation has been shown to stimulate hair growth on the bald spot of the back of the head in men, and, in women, it can increase hair growth in the forehead area. It is believed to be most effective in persons with recent onset of hair loss due to androgenetic alopecia, and relatively small areas of hair loss. It is typically less effective when hair loss is long-standing or large in area. Thus, early use of minoxidil is indicated to prevent progression of small areas of pattern baldness. Generic versions of the topical formulation are also available in various concentrations. The inventors have surprisingly found that minoxidil may be used for yet another therapeutic purpose: for the treatment of cancer, and, in particular, for the treatment of brain tumors. Minoxidil sulfate and Pinacidil were found to have similar potency as other anti-tumor and chemotherapeutic drugs (see table 2). While not wishing to be bound to any particular theory, the inventors believe that minoxidil increases cell death by necrosis and apoptosis.

A number of other ATP-dependent potassium channel agonists are known to those of skill in the art and may be used, either alone or in combination with still further ATP-dependent potassium channel agonists, in connection with alternate embodiments of the present invention. See, e.g., K. Oe et al., "Modulation of norepinephrine release by ATP-dependent K(+)-channel activators and inhibitors in guinea-pig and human isolated right atrium," Cardiovasc. Res., 43(1):125-134 (July 1999). By way of example, in one embodiment of the present invention, cromakalim may be used. Similar to minoxidil, cromakalim was originally used in the treatment of high blood pressure, but has also been found to be effective in promoting hair growth. Further examples of ATP-dependent potassium channel agonists are numerous, and need not have similar efficacy with respect to hypertension and/or hair growth as minoxidil in order to be suitable for use in accordance with the present invention. For instance, diazoxide (used in the treatment of hypoglycemia) is an ATP-dependent potassium channel agonist that may be used in connection with alternate embodiments of the present invention. Additional examples of ATP-dependent potassium channel agonists include levcromakalim, emakalim, bimakalim, celikalim, rimakalim, pinacidil, aprikalim, picartamide, KCO912, and nicorandil. Indirect agonists of the ATP-dependent potassium channel may also be used. Examples of indirect agonists include adenylyl cyclase activators, activators of cyclic AMP (cAMP) dependent protein kinases, and agents that increase the formation of cAMP or prevent the breakdown of cAMP. Further examples of ATP-dependent potassium channel agonists may be found in U.S. patent application Ser. No. 10/938,674, "Potassium Channel Mediated Delivery of Agents Through the Blood-Brain Barrier," herein incorporated by reference in its entirety as though fully set forth. Additionally, included among useful ATP-dependent potassium channel agonists are chemical analogs or salt forms that still have activity as an ATP-dependent potassium channel agonist. Many other ATP-dependent potassium channel agonists will be readily recognized by those of skill in the art and can be used in connection with the present invention without undue experimentation.

The ATP-dependent potassium channel agonists may be administered to a mammal (e.g., a human) by any conventional technique in accordance with various embodiments of the present invention for the treatment of a disease condition, such as cancer and/or a tumor; in particular, brain cancer and/or a brain tumor. The ATP-dependent potassium channel agonists may be delivered in an amount sufficient to alleviate or cure the disease condition and/or to achieve beneficial results. The ATP-dependent potassium channel agonists may be administered by any conventional delivery route, either alone or in combination with other chemotherapeutic agents, antiproliferative agents or cancer therapy (e.g., radiation therapy, vaccination therapy, and enhancement of the blood-brain barrier or the blood-tumor barrier).

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene). Additional examples of specific antiproliferative agents include, but are not limited to levamisole, gallium nitrate, granisetron, sargramostim strontium-89 chloride, filgrastim, pilocarpine, dexrazoxane, and ondansetron.

Vaccination therapy has been studied for its role in treating cancer. (See, e.g., R. P. Glick et al., "Intracerebral versus subcutaneous immunization with allogeneic fibroblasts genetically engineered to secrete interleukin-2 in the treatment of central nervous system glioma and melanoma," Neurosurg., 412-498 (1997); L. M. Liau et al., "Treatment of intracranial gliomas with bone marrow-derived dendritic cells pulsed with tumor antigens," J. Neurosurg., 90: 1115 (1999); and J. S. Yu et al., "Vaccination of malignant glioma patients with peptide-pulsed DC elicits systemic cytotoxicity and intracranial T-cell infiltration," Cancer Res., 61942 (2001).) As a further embodiment, the ATP-dependent potassium channel agonist may be administered in conjunction with such vaccination therapies (i.e., administering an ATP-dependent potassium channel agonist prior to, concurrent with and/or after a vaccination therapy). See PCT Publication WO 2005/043155, "System and Method for the Treatment of Cancer, Including Cancers of the Central Nervous System," herein incorporated by reference in its entirety as though fully set forth.

While the administration of minoxidil sulfate and/or other ATP-dependent potassium channel agonists alone elicit in vitro and in vivo anti-tumor activity, and without wishing to be bound by any particular theory, the inventors believe that further enhancement of in vivo anti-tumor activity by minoxidil sulfate and/or other ATP-dependent potassium channel agonist may be accomplished by enhancing the blood-brain barrier ("BBB") and/or the blood-tumor barrier ("BTB") permeability. Thus, additional embodiments provide for the administration of the ATP-dependent potassium channel agonist in conjunction with an agent to enhance the permeability of the BBB and/or the BTB, to assist in increasing the concentration of the ATP-dependent potassium channel agonist in the brain tumor. For example, U.S. patent application Ser. No. 10/938,674, "Potassium Channel Mediated Delivery of Agents through the Blood-Brain Barrier," herein incorporated by reference in its entirety as though fully set forth, provides suitable agents to enhance the permeability of the BBB and/or the BTB and suitable methods to administer the agents in conjunction with a chemotherapeutic agent.

In various embodiments, the present invention provides pharmaceutical compositions including a pharmaceutically acceptable excipient along with a therapeutically effective amount of an ATP-dependent potassium channel agonist or a salt or chemical analog thereof; for example, minoxidil or minoxidil sulfate. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including but not limited to intraorbital, infusion, intracarotid, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Delivery may also be made by intratumoral injection through a surgical incision, for example, through a craniotomy for a brain tumor. Typically, but not necessarily, surgical resection of the tumor is done, if possible, before injection of the ATP-dependent potassium channel agonist into any remaining tumor mass containing malignant cells. Another delivery method is stereotactic injection of the ATP-dependent potassium channel agonists or salts or chemical analogs thereof into the tumor at a site having pre-established coordinates.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include, but are not limited syrup, peanut oil, olive oil, glycerin, saline, alcohols and water. Solid carriers include, but are not limited to starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o., filled into a soft gelatin capsule, or through an injection.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins P A, USA) (2000).

Dosages may also be as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described. In animal models such mice and rats, the typical dosage of an effective amount of an ATP-dependent potassium channel agonist or a salt or chemical analog thereof, to treat cancer may be from about 50 to about 250 µg/kg/minute administered continuously for about 15 minutes. Particularly effective dosages of an ATP-dependent potassium channel agonist or a salt or chemical analog thereof, to treat cancer may be from about 100 to about 180 µg/kg/minute administered continuously for about 15 minutes. In one embodiment, a dosage of an effective amount of an ATP-dependent potassium channel agonist or a salt or chemical analog thereof, to treat cancer may be 180 µg/kg/minute administered continuously for about 15 minutes. One of skill in the art will appreciate that the ATP-dependent potassium channel agonist or a salt or chemical analog thereof may be administered continuously for a period less than about 15 minutes. In such instances, one of skill in the art can adjust the concentration of the ATP-dependent potassium channel agonist or a salt or chemical analog thereof, for a total dosage in the aforementioned ranges. In other embodiments, a single bolus of an ATP-dependent potassium channel agonist or a salt or chemical analog thereof, may be administered to treat cancer. In one embodiment the single bolus may be from about 750 µg/kg to about 3750 µg/kg. In another embodiment the single bolus may be from about 1500 µg/kg to about 2700 µg/kg. In a further embodiment the single bolus may be about 2700 µg/kg.

For human subjects, a typical dosage of an effective amount of an ATP-dependent potassium channel agonist or a salt or chemical analog thereof for human subjects may be from about 5 to about 35 mg per day. The administration of the about 5 to about 35 mg of an ATP-dependent potassium channel agonist or a salt or chemical analog thereof, per day may be via a single bolus or administered continuously for up to about 15 minutes. In instances of continuous administration of the ATP-dependent potassium channel agonist or a salt or chemical analog thereof, one of skill in the art can adjust the concentration of the ATP-dependent potassium channel agonist or a salt or chemical analog thereof, for a total dosage in the aforementioned ranges. The actual dosage for a human will depend upon the judgment of the physician, the condition of the patient, any hypotensive effects on the patient and the effectiveness of the therapeutic method.

The present invention is also directed to a kit for treating cancer; for example, brain tumors. The kit is useful for practicing the inventive method of treating cancer by increasing cell death. The kit is an assemblage of materials or components, including at least one of the inventive compositions. Thus, in some embodiments the kit contains a composition including an ATP-dependent potassium channel agonist or a salt or chemical analog thereof; for example, minoxidil or minoxidil sulfate, as described above.

The exact nature of the components configured in the inventive kit depends on its intended purpose. For example, some embodiments are configured for the purpose of treating cancer, (e.g., brain tumors) by increasing cell death. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as inducing tumor cell death to treat cancer. For example, instructions for use may include instructions to administer a therapeutically effective amount of the ATP-dependent potassium channel agonist to the mammal. Optionally, the kit also contains other useful components, such as, diluents, buffers, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in treating cancer. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing ATP-dependent potassium channel agonists a salt or chemical analog thereof; for example, minoxidil or minoxidil sulfate. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

While not wishing to be bound by any particular theory, the inventors believe that there may be an independent effect on cell apoptosis by potassium channel activation. Thus, the inventors examined the in vitro effect of several ATP-dependent potassium channel agonists on cell viability in a wide range of tumor and normal cells. In the inventors' cytotoxic screening using a cell proliferation assay (WST-1 assay; Roche Diagnostics), the inventors found that minoxidil sulfate was highly effective as a cytotoxic agent against several tumor cell lines (C6 rat glioma, U87 human glioma, and HT-29 human colon cancer) while two other KATP channel agonists were less effective. It should also be noted that endothelial cells (non-cancer cells) are fairly resistance to the cytotoxic effect of all three ATP-dependent potassium channel agonists tested.

Table 1 depicts the in vitro effect of KATP channel agonists on cell viability in a range of tumor and normal cells. The cytotoxic screening assay (WST-1 assay; Roche Diagnostics) results shown are the effective KATP channel agonist concentration ($\mu M$) required for 50% cell death (EC50) after exposure to the same for 24 hours. Indicated percentages are the percent viable cells remaining after treatment with 1000 $\mu M$ of KATP channel agonists.

TABLE 1

Effective concentration ($\mu M$) of KATP channel agonists for 50% cell death ($EC_{50}$) after treatment for 24 hours.

| | K(ATP) Agonists | | |
|---|---|---|---|
| | Min. Sulfate | KCO912 | Pinacidil |
| RG2 Glioma | 810 | >1000 (81%) | >1000 (69%) |
| 9L Glioma | >1000 (51%) | | 790 |
| C6 Glioma | 130 | | >>1000 (93%) |
| GL-26 Glioma | 595 | >1000 (69%) | 210 |
| U87 Glioma | 308 | >>1000 (107%) | >1000 (77%) |
| MDA-231 Breast Cancer | 930 | 126 | 220 |
| CRL5904 NSC Lung Cancer | >1000 (89%) | >>1000 (101%) | >1000 (79.5%) |
| HT-29 Colon Cancer | 360 | >1000 (83%) | >1000 (74%) |
| DNTC-1 Astrocytes | 110 | | |
| HBMVEC Endothelial | >1000 (84%) | >1000 (66%) | >>1000 (106%) |

Indicated percentages are the percentage of viable cells remaining after treatment with 1000 $\mu M$ of KATP channel agonists.

Example 2

GL26 drug cytotoxicity ($EC_{50}$, concentrations giving 50% killing) screens were performed with the results depicted in Table 2.

TABLE 2

Sensitivity of unmodified GL26 cells to chemotherapeutic agents

| Drug (125-1000 µM) | $EC_{50}$ (µM) |
|---|---|
| Temodar | >1000 |
| Carboplatin | 310 |
| Adriamycin | <125 |
| Methotrexate | >1000 |
| Minoxidil Sulfate | 595 |
| Pinacidil | 210 |

Example 3

In Vivo Model of T Cell-Induced Glioma Chemosensitivity

GL26 glioma cells were implanted intracranially into T cell-deficient (nude) or syngeneic wild-type (C57Bl/6) mice, which were treated with a chemotherapeutic drug alone or with vaccination using GL26 lysate-pulsed DC2.4 dendritic cells. Minoxidil sulfate enhanced survival in wild-type hosts, eliciting a survival increase with or without vaccine treatment. (FIG. 1).

Example 4

Survival is Prolonged by Minoxidil Sulfate

Chemosensitivity was modeled by growth of the GL26 glioma in syngeneic C57BL/6 (B6), vaccinated B6, and T cell-deficient nude mice. Tumor implantation was followed by chemotherapeutic drug treatment and/or DC vaccination. Chemotherapy prolonged survival in B6, but not in nude hosts, suggesting that T cell activity chemosensitizes GL26 gliomas in vivo (FIGS. 2a and 2b). Not wishing to be bound by any particular theory the inventors believe that survival of GL26-bearing B6 hosts closely paralleled that of GBM patients receiving post-vaccine chemotherapy, while nude mouse survival resembled that of GBM patients receiving single therapies. Notably, survival of B6 hosts was prolonged by chemotherapy regardless of vaccination, whereas chemosensitization (with chemotherapeutic drugs other than minoxidil) was seen only after DC vaccination in human GBM patients. (See Wheeler, C. J., et al., "Clinical responsiveness of glioblastoma multiforme to chemotherapy after vaccination," Clin. Cancer Res. 10:5316-5326 (2004).) This difference may be due to the distinct drugs used, to superior endogenous immune activity in mice (which influences intrinsic tumor behavior) relative to patients, or to inefficient DC vaccination.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

We claim:

1. A method for therapeutically treating a brain tumor selected from the group consisting of glioma, glioblastoma, glioblastoma multiforme, astrocytoma and combinations thereof in a mammalian subject in need thereof, consisting of:
providing a composition consisting of minoxidil or a salt thereof and a pharmaceutically acceptable carrier; and
administering a therapeutically effective amount of the composition to the mammalian subject to treat the brain tumor.

2. The method of claim 1, wherein the brain tumor is glioma.

3. The method of claim 1, wherein the salt of minoxidil is minoxidil sulfate.

4. The method of claim 1, wherein the brain tumor is glioblastoma.

5. The method of claim 1, wherein the brain tumor is glioblastoma multiforme.

6. The method of claim 1, wherein the brain tumor is astrocytoma.

7. The method of claim 1, wherein the therapeutically effective amount of the composition is administered via a single bolus.

8. The method of claim 1, wherein the therapeutically effective amount of the composition is administered via a continuous administration for up to about 15 minutes.

9. The method of claim 1, wherein the therapeutically effective amount of the composition is about 5-35 mg per day of minoxidil or the salt thereof.

10. The method of claim 1, wherein the composition consists of minoxidil and the pharmaceutically acceptable carrier.

11. The method of claim 1, wherein the composition consists of minoxidil sulfate and the pharmaceutically acceptable carrier.

12. The method of claim 1, wherein the mammalian subject is a human subject.

* * * * *

UNITED STATES PATENT AND TRADEMARK OFFICE
CERTIFICATE OF CORRECTION

| | |
|---|---|
| PATENT NO. | : 7,705,010 B2 |
| APPLICATION NO. | : 11/813461 |
| DATED | : April 27, 2010 |
| INVENTOR(S) | : Keith L. Black et al. |

It is certified that error appears in the above-identified patent and that said Letters Patent is hereby corrected as shown below:

In column 1, line 11 after the cross-reference to related applications but before the "Field of the Invention" section, please insert the following:

--FEDERAL SUPPORT
The U.S. Government has a paid-up license in this invention and the right in limited circumstances to require the patent owner to license others on reasonable terms as provided for by the terms of Grant Nos. NS046388 and NS32103 awarded by the National Institutes of Health.--

Signed and Sealed this
Twelfth Day of February, 2013

Teresa Stanek Rea
*Acting Director of the United States Patent and Trademark Office*